United States Patent [19]

Simonzi

[11] Patent Number: 4,917,134
[45] Date of Patent: Apr. 17, 1990

[54] DISPOSABLE MEDICINAL APPLICATOR PAD

[76] Inventor: Gloria Simonzi, 5890 38th Ave. N. Apt. 101-A, St. Petersburg, Fla. 33710

[21] Appl. No.: 391,976

[22] Filed: Aug. 10, 1989

[51] Int. Cl.⁴ .............................................. A45D 40/26
[52] U.S. Cl. ..................... 132/320; 206/210; 401/200
[58] Field of Search ......... 132/320; 15/209 R, 209 E, 15/212; 206/438, 439, 440, 823, 209, 210, 363; 401/200

[56] References Cited

U.S. PATENT DOCUMENTS

| | | | |
|---|---|---|---|
| 1,330,372 | 2/1920 | Grossman | 206/823 |
| 1,468,164 | 9/1923 | McCarty | 401/200 |
| 1,791,351 | 2/1931 | Chase | 132/320 |
| 1,836,833 | 12/1931 | Ames | 401/200 |
| 1,968,696 | 7/1934 | Mar | 15/209 R |
| 1,993,174 | 3/1935 | Le Coney | 15/209 R |
| 2,520,343 | 8/1950 | Saum | 401/200 |
| 2,779,465 | 1/1957 | Anderson | 15/209 R |
| 2,932,839 | 4/1960 | Flanigan et al. | 15/209 R |

FOREIGN PATENT DOCUMENTS

418276  9/1910  France .................. 401/200

Primary Examiner—Gene Mancene
Assistant Examiner—Michael Lynch
Attorney, Agent, or Firm—Arthur W. Fisher, III

[57] ABSTRACT

A disposable medicinal applicator pad capable of being reshaped from a substantially flat configuration for storage to a puff configuration for use on a patient and a applicator pad dispenser for storing and dispensing a plurality of disposable medicinal applicator pads when in the substantially flat configuration, each disposable medicinal applicator pad comprises a pair of porous, absorbent membranes secured together by a continuous thread with a basting about the periphery thereof to retain a medicinal powder therebetween, the continuous thread includes a loop or grasping element whereby the continuous thread may be drawn or gathered about the periphery of the pair of porous, absorbent membranes by pulling or drawing the grasping element to reshape the disposable medicinal applicator pad to the puff configuration such that the medicinal powder may be applied to a specific area of the patient's body to reduce excoriation and maintain the normal pH level.

14 Claims, 1 Drawing Sheet

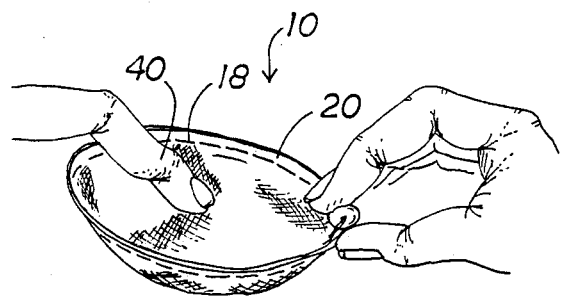
Fig_2
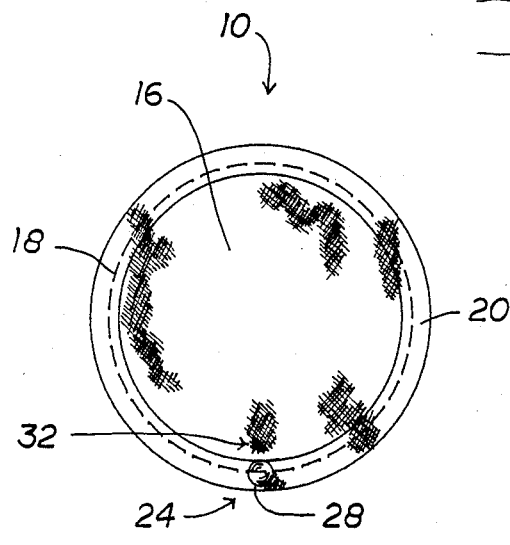
Fig_1
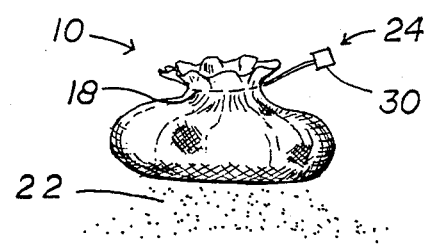
Fig_3
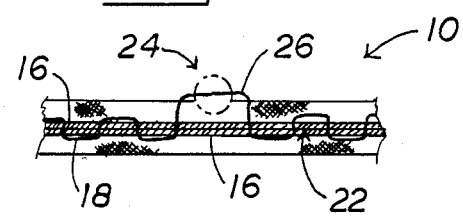
Fig_4
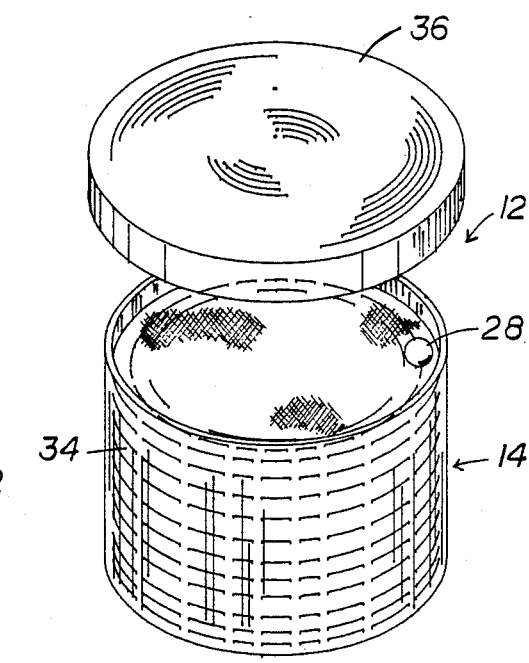
Fig_5
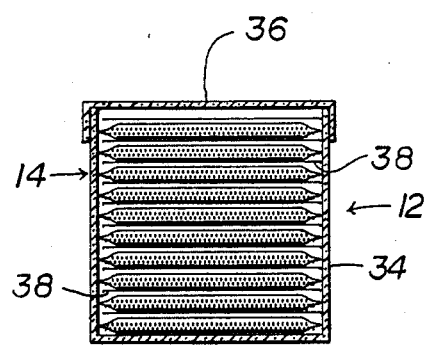
Fig_6

DISPOSABLE MEDICINAL APPLICATOR PAD

BACKGROUND OF THE INVENTION

1. Field of the Invention

A disposable medicinal applicator pad and an applicator pad dispenser for storing and dispensing a plurality of such disposable medicinal applicator pads wherein the disposable medicinal applicator pads are capable of being reshaped from a flat or storage configuration and a puffed or application configuration.

2. Description of the Prior Art

Medicinal powders are widely used in patient care to restore skin integrity and maintain proper pH level of the patient's skin. Commonly medicinal powders are sprinkled on a specific area of the patient's body. Such uncontrolled application often results in caking the powder to the applied area with obvious attendant deleterious effect to the skin. In addition, the use of talc and similar powders is generally prohibited in critical care units and other environmentally sensitive areas to preclude damage to the various machines found in such areas. Thus there is a clear need for means to apply a predetermined or controlled amount of medicinal powder to a specific, limited areas of the patient.

U.S. Pat. No. 1,444,741 teaches a main powder puff having a receptacle thereon, draw strings for closing the receptacle and applicator puffs at the ends of the draw strings. The applicator puffs are confined within the receptacle when the latter is closed whereby the draw strings function as supporting loops on the main powder puff.

U.S. Pat. No. 1,791,351 shows an applicator pad for use in applying facial powder and the like comprising a plurality of substantially flat elements. Each element includes an integral pull tab projecting from the peripheral edge and means uniting adjacent elements.

U.S. Pat. No. 1,834,833 discloses an applicator pad for applying cosmetics comprising a piece of fabric, a coating of cosmetic on one surface of the fabric and a protective covering whereby portions of the fabric and the protective covering may be separated to expose the coating of cosmetic.

U.S. Pat. No. 1,424,649 shows a powder puff comprising a pair of loosely fabricated pieces of material connected throughout the greater portion of their length to form a receptacle and a finger receiving handle comprising a strap having opposite ends attached to the two pieces.

U.S. Pat. No. 1,522,435 teaches a powder puff comprising layers of material each having a substantially circular body portion and an integral flap portion.

SUMMARY OF THE INVENTION

The present invention relates to a disposable medicinal applicator pad capable of being reshaped from a substantially flat configuration for storage to a puff configuration for use on a specific area of the patient. The invention may further include a applicator pad dispenser for storing and dispensing a plurality of the disposable medicinal applicator pads in stacked array when in the flat configuration.

Each disposable medicinal applicator pad comprises a pair of porous, absorbent members secured together by a continuous thread sewn about the periphery thereof to retain a medicinal powder therebetween. The continuous thread is attached to the porous, absorbent membranes with a basting. A grasping element is formed in the continuous thread for grasping the individual disposable medicinal applicator pads for removal from the applicator pad dispenser and to reshape the disposable medicinal applicator pad from the flat configuration to the puff configuration as described more fully hereinafter.

The applicator pad dispenser comprises an applicator pad housing having a cap or cover removably mounted thereon. A plurality of the disposable medicinal applicator pads may be stored in the flat configuration in stacked array. A nonporous element or membrane may be disposed between adjacent disposable medicinal applicator pads to retain the predetermined quantity of powder within each of the disposable medicinal applicator pads when stored.

Initially the cap or cover is removed from the applicator pad housing. The user may then withdraw or extract the upper-most disposable medicinal applicator pad from the applicator pad housing by grasping the grasping element between a thumb and corresponding index finger. Then with the disposable medicinal swab on a flat surface, the user then places one or more fingers of the opposite hand in the center of the disposable medicinal applicator pad and pulls the continuous thread while holding the disposable medicinal powder applicator pad in place. This gathers or draws the continuous thread about the periphery of the porous, absorbent members to form the puff configuration. In the puff configuration, the user then applies the predetermined quantity of medicinal powder to a specific area of the patient without over-application as well as absorbing any body fluid or moisture from the patient's skin to prevent excoriation and maintain the proper pH level.

The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a fuller understanding of the nature and object of the invention, reference should be had to the following detailed description taken in connection with the accompanying drawings in which:

FIG. 1 is a top view of the disposable medicinal applicator pad in the substantially flat configuration.

FIG. 2 is a perspective view of the disposable medicinal applicator pad in transition from the substantially flat configuration to the puff configuration.

FIG. 3 is a side view of the disposable medicinal applicator pad in the puff configuration.

FIG. 4 is a partial detail view of the continuous thread and pair of the porous, absorbent membranes.

FIG. 5 is an exploded view of the applicator pad dispenser with a plurality of the disposable medicinal applicator pads disposed in stacked array therein.

FIG. 6 is a cross-sectional side view of the applicator pad dispenser with a plurality of the disposable medicinal applicator pads disposed in stacked array therein.

Similar reference characters refer to similar parts throughout the several views of the drawings.

DETAILED DESCRIPTION OF THE PREFERRED EMBODIMENT

FIGS. 1 through 3, the present invention relates to a disposable medicinal applicator pad generally indicated as 10 capable of being reshaped from a substantially flat configuration for storage as shown in FIG. 1 to a puff configuration as shown in FIG. 3 for use on a specific area of a patient. The disposable medicinal applicator pad 10 is particularly suitable to prevent skin excoriation caused by incontinence of feces and urine or other body secretions as well as restore the proper pH balance. Of course, the invention is equally useful on sores, wounds and minor skin irritations.

As shown in FIGS. 5 and 6 the invention may further include a applicator pad dispenser generally indicated as 12 for storing and dispensing a plurality of the disposable medicinal applicator pads 10 in stacked array 14 when in the flat configuration.

As shown in FIGS. 1 and 4, each disposable medicinal applicator pad 10 comprises a pair of substantially circular porous, absorbent members each indicated as 16 secured together by a continuous thread 18 disposed about the periphery 20 thereof to retain a predetermined amount of medicinal powder 22 therebetween. The medicinal powder is preferably 6 parts of corn starch to one part boric acid powder. As shown in FIGS. 1 and 4, the continuous thread 18 attached to the substantially circular porous, absorbent membranes 16 in a basting stitch. There are three or less stitches per inch. A grasping means generally indicated as 24 is formed on the continuous thread 18 for grasping the individual disposable medicinal applicator pads 10 for removal from the applicator pad dispenser 12 and to facilitate gathering of the continuous thread 18 and the disposable medicinal applicator pad 10 from the flat configuration as shown in FIG. 1 to the puff configuration as shown as FIG. 3 as described more fully hereinafter. The grasping means 24 may comprise a loop 26 formed in the continuous thread 18, a bead 28 attached to the continuous thread 18 or a substantially flat member 30 as shown in FIGS. 4, 1 and 3 respectively. A visual indicia 32 may be found on the upper substantially circular porous, absorbent member 16 adjacent the grasping means 24.

The applicator pad dispenser 12 comprises a substantially cylindrical applicator pad housing 34 with substantially cylindrical cover or cap 36 removably mounted thereof. A plurality of the disposable medicinal applicator pads 10 are stored in the flat configuration in stacked array 14 as shown in FIGS. 5 and 6. A nonporous element or membrane 38 may be disposed between adjacent disposable medicinal applicator pads 10 to retain the predetermined quantity powder 22 within each of the disposable medicinal applicator pads 10 when stored.

Initially with the substantially cylindrical cap or cover 36 is removed from the top of the substantially cylindrical applicator pad housing 34. The user then withdraws or extracts the upper-most disposable medicinal applicator pad 10 from the substantially cylindrical applicator pad housing 34 by grasping the grasping means 24 between the thumb and corresponding index finger. Then with the disposable medicinal applicator pad 10 supported on a flat surface as shown in FIG. 2, the user then places one or more fingers 40 of the opposite hand in the center of the disposable medicinal applicator pad 10 and gathers the continuous thread 18 by pulling the grasping means 24 while holding the disposable medicinal applicator pad 10 in place. This draws the continuous thread 18 about the periphery 20 of the substantially cylindrical porous, absorbent membranes 16 to form the puff configuration as shown in FIG. 3. In the puff configuration, the user applies the predetermined quantity of medicinal powder 22 to a specific area of the patient. Thus the desired amount of medicinal powder 22 is applied directly to the desired area without over-application while absorbing moisture from the patient's skin to prevent excoriation and maintain the proper pH level.

Of course, the upper-most disposable medicinal applicator pad 10 may be transformed from the flat configuration to the puff configuration while still within the substantially cylindrical applicator pad housing 34.

It will thus be seen that the objects set forth above, among those made apparent from the preceding description are efficiently attained and since certain changes may be made in the above construction without departing from the scope of the invention, it is intended that all matter contained in the above description or shown in the accompanying drawing shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

What is claimed is:

1. A disposable medicinal applicator pad capable of being reshaped from a substantially flat configuration for storage to a puffed configuration for use with a patient, each said disposable medicinal applicator pad comprises a pair of porous, absorbent membranes secured together by a continuous thread attached about the periphery thereof to retain a predetermined quantity of powder therebetween, an applicator pad grasping means is formed on said continuous thread whereby the continuous thread may be drawn or gathered about the periphery of said pair of porous, absorbent membranes by pulling or drawing said grasping means reshaping said disposable medicinal applicator pad to the puffed configuration such that the medicinal powder may be applied to a specific area of the patient's body to reduce excoriation and maintain the normal pH level.

2. A disposable medicinal applicator pad of claim 1 wherein each said porous, absorbent membrane comprises a substantially circular configuration.

3. The disposable medicinal applicator pad of claim 2 wherein the porous thread is attached to said substantially circular porous, absorbent membranes by a basting stitch.

4. The disposable medicinal applicator pad of claim 3 wherein said continuous thread comprises three or less stitches per inch.

5. The disposable medicinal applicator pad of claim 1 wherein said grasping means comprises a loop formed in one continuous thread.

6. The disposable medicinal applicator pad of claim 5 further including a visual indicia formed on one of said porous, absorbent membranes adjacent said loop.

7. The disposable medicinal applicator pad of claim 1 wherein said grasping means comprises a bead attached to said continuous thread.

8. The disposable medicinal applicator pad of claim 7 wherein said bead comprises a spherical configuration.

9. The disposable medicinal applicator pad of claim 1 wherein said grasping means comprises a substantially flat member.

10. The disposable medicinal applicator pad of claim 1 wherein said powder comprises preferably 6 parts of corn starch to one part of boric acid powder.

11. The disposable medicinal applicator pad of claim 1 further including a plurality of said disposable medicinal applicator pads and a pad dispenser configured to store and dispense said plurality of said disposable medicinal applicator pads.

12. The disposable medicinal applicator pad of claim 11 further including said applicator pad dispenser comprises an applicator pad housing and an applicator pad cover removably mounted thereon.

13. The disposable medicinal applicator pad of claim 12 wherein said applicator pad housing and said applicator pad cover are of a substantially cylindrical configuration.

14. The disposable medicinal applicator pad of claim 11 wherein said plurality of medicinal applicator pads are separated by a nonporous element disposed between adjacent pads when stored in said dispenser.

* * * * *